United States Patent
Pabich et al.

(10) Patent No.: US 9,187,789 B2
(45) Date of Patent: Nov. 17, 2015

(54) POLYNUCLEOTIDES FOR THE AMPLIFICATION AND DETECTION OF CHLAMYDIA TRACHOMATIS AND NEISSERIA GONORRHOEAE

(71) Applicant: ABBOTT MOLECULAR INC, Des Plaines, IL (US)

(72) Inventors: Edward K. Pabich, Northbrook, IL (US); Ronald L. Marshall, Pleasant Prairie, WI (US); Hong Yu, Long Grove, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 14/055,791

(22) Filed: Oct. 16, 2013

(65) Prior Publication Data

US 2014/0120536 A1 May 1, 2014

Related U.S. Application Data

(62) Division of application No. 12/764,301, filed on Apr. 21, 2010, now Pat. No. 8,580,495, which is a division of application No. 10/292,420, filed on Nov. 12, 2002, now Pat. No. 7,807,802.

(51) Int. Cl.
*C12Q 1/68* (2006.01)
*C07H 21/04* (2006.01)

(52) U.S. Cl.
CPC ............... *C12Q 1/689* (2013.01); *C07H 21/04* (2013.01)

(58) Field of Classification Search
CPC ..................................................... C12Q 1/689
See application file for complete search history.

(56) References Cited

U.S. PATENT DOCUMENTS

| | | | |
|---|---|---|---|
| 5,162,199 A | 11/1992 | Stern et al. | |
| 5,427,930 A | 6/1995 | Birkenmeyer et al. | |
| 5,453,355 A | 9/1995 | Birkenmeyer et al. | |
| 5,550,040 A | 8/1996 | Purohit et al. | |
| 5,691,136 A | 11/1997 | Lupski et al. | |
| 6,077,669 A | 6/2000 | Little et al. | |
| 7,807,802 B2 | 10/2010 | Pabich et al. | |

FOREIGN PATENT DOCUMENTS

| | | | |
|---|---|---|---|
| EP | 336412 | A2 | 10/1989 |
| EP | 337896 | A1 | 10/1989 |
| EP | 0404161 | A2 | 12/1990 |
| EP | 428693 | A1 | 5/1991 |
| EP | 546761 | A1 | 6/1993 |
| EP | 630971 | A2 | 12/1994 |
| EP | 692540 | A2 | 1/1996 |
| EP | 823485 | A1 | 2/1998 |
| EP | 875583 | A2 | 11/1998 |
| EP | 0919633 | A2 | 6/1999 |
| EP | 925789 | A1 | 6/1999 |
| EP | 630971 | B1 | 4/2001 |
| EP | 1103622 | A2 | 5/2001 |
| WO | 9015159 | A2 | 12/1990 |
| WO | 9213871 | A1 | 8/1992 |
| WO | 9300447 | A1 | 1/1993 |
| WO | 9410571 | A1 | 5/1994 |
| WO | 9711181 | A1 | 3/1997 |
| WO | 9810101 | A1 | 3/1998 |
| WO | 9855646 | A1 | 12/1998 |
| WO | 9917741 | A1 | 4/1999 |
| WO | 9923250 | A2 | 5/1999 |
| WO | 9924606 | A2 | 5/1999 |
| WO | 9928475 | A2 | 6/1999 |
| WO | 9957280 | A2 | 11/1999 |
| WO | 0003003 | A2 | 1/2000 |
| WO | 0006739 | A2 | 2/2000 |
| WO | 0006740 | A1 | 2/2000 |
| WO | 0006741 | A1 | 2/2000 |
| WO | 0006742 | A2 | 2/2000 |
| WO | 0006743 | A2 | 2/2000 |
| WO | 0011183 | A2 | 3/2000 |
| WO | 0022430 | A2 | 4/2000 |
| WO | 0023595 | A1 | 4/2000 |
| WO | 0024765 | A2 | 5/2000 |
| WO | 0024901 | A1 | 5/2000 |
| WO | 0024902 | A1 | 5/2000 |
| WO | 0026376 | A1 | 5/2000 |
| WO | 0032784 | A1 | 6/2000 |
| WO | 0032794 | A2 | 6/2000 |
| WO | 0037494 | A2 | 6/2000 |
| WO | 0066791 | A1 | 11/2000 |
| WO | WO 02/055739 | * | 7/2002 |
| WO | 2004043227 | A2 | 5/2004 |

OTHER PUBLICATIONS

GenBank accession No. X52369 (Feb. 1993).*
GenBank accession No. X52371 (Feb. 1993).*
Piatek, A.S. et al., Nature Biotechnol., vol. 16, pp. 359-363 (1998).*
Bhat K.S., et al., "N.gonorrhoeae opaF gene for opacity protein", 1995.
Bhat, K.S. et al., "The opacity proteins of Neisseria gonorrhoeae strain MS11 are encoded by a family of 11 complete genes", Mol. Microbiol., 5, 1889-1901, 1991.
Buck G.A., et al., "Design Strategies and Performance of Custom DNA Sequencing Primers," BioTechniques, 1999, vol. 27 (3), pp. 528-536.
European Search Report for Application No. EP10158028, mailed on Apr. 23, 2010, 2 pages.
Little, M. C. et al., "Strand displacement amplification and homogeneous real-time detection incorporated in a second-generation DNA probe system, BDProbeTecET", Clin. Chemistry, 45, 777-784, 1999.
Stephens, R.S. et al., "Genome sequence of an obligate intracellular pathogen of humans: chlamydia trachomatis," Science (1998) 282:754-759.

* cited by examiner

*Primary Examiner* — Teresa E Strzelecka
(74) *Attorney, Agent, or Firm* — Lisa V. Mueller; Michael Best & Friedrich LLP

(57) ABSTRACT

Polynucleotides useful for detecting *Chlamydia trachomatis* and/or *Neisseria gonorrhoeae* in a test sample, kits, a nucleic acid amplification method and detection method including the same.

9 Claims, No Drawings

POLYNUCLEOTIDES FOR THE AMPLIFICATION AND DETECTION OF CHLAMYDIA TRACHOMATIS AND NEISSERIA GONORRHOEAE

CROSS-REFERENCE TO RELATED APPLICATIONS

This is a divisional of U.S. patent application Ser. No. 12/764,301, filed on Apr. 21, 2010, which is a divisional of U.S. patent application Ser. No. 10/292,420, filed on Nov. 12, 2002, now issued as U.S. Pat. No. 7,807,802, the contents of all of which are fully incorporated herein by reference.

SEQUENCE LISTING

The instant application contains a Sequence Listing which has been submitted electronically in ASCII format and is hereby incorporated by reference in its entirety. Said ASCII copy, created on Jan. 6, 2014, is named 6873USD2_SL.txt and is 3,255 bytes in size.

FIELD OF THE INVENTION

The present invention relates to *Chlamydia trachomatis* and *Neisseria gonorrhoeae*. In particular the invention relates to polynucleotides and methods for amplifying and detecting *Chlamydia trachomatis* and *Neisseria gonorrhoeae*.

BACKGROUND OF THE INVENTION

*Chlamydia trachomatis* (*C. trachomatis* or CT) and *Neisseria gonorrhoeae* (*N. gonorrhoeae* or NG) are the causative agents of common sexually transmitted diseases. CT causes venereal lymphogranuloma, various inflammatory pathologies of the male and female urogenital systems, and trachoma, a chronic disease that affects 500 million people and can lead to blindness. When not precociously diagnosed and treated by adequate therapy, CT-induced urethritis and cervicitis may led to a variety of chronic inflammations, such as, e.g., vaginitis, salpingitis and pelvic inflammation which may result in sterility and extrauterine pregnancy. Furthermore, the new born from infected mothers may contract pulmonary and/or ocular infections during delivery.

*N. gonorrhoeae*, the pathogen of gonorrhoea, manifests itself as a purulent inflammation and swelling of the urethra in males. These symptoms occur in 90% of cases of infection. If left untreated, the infection can ascend and after several weeks produce symptoms of prostatitis. In women, no or only slight symptoms occur in 50% of cases of infection. The infection primarily affects the cervix, but also the urethra. In 10 to 15% of women, the infection spreads to the fallopian tubes and can also lead to sterility. Since the course of the infections is often asymptomatic, many carriers contribute unknowingly to the spread of the disease.

Considering the impact that these two organisms have, rapid and specific diagnostic tests are of utmost importance. Diagnosis based on selective growth of the pathogenic bacteria has been the standard, but cell culturing is time-consuming and many clinical isolates are difficult to grow in vitro. Infection with bacteria results in the formation of a variety of antibodies with serogroup, species, subspecies, serovar (serotype) and auxotype specificity. Sera from patients with genital tract infections have been used to diagnose CT and NG infection, however assays based on serological markers are by nature non-quantitative and subject to difficulties in interpretation. For example, antibody titres may be undetectable in acute infections (false negative), may persist in uninfected individuals with a past history of infection (false positive), may yield a false-positive indication due to the presence of cross-reacting species (e.g., respiratory infection by different *Chlamydia* species), or may not develop at all (false negative) depending on other factors (Ngeow, 1996, Ann Acad Med Singapore 25:300; Black et al., 1991, J Clin Microbiol 29:1312). For these reasons, serology alone is inadequate for the diagnosis of CT and NG infections.

Bacterial infections may also be diagnosed by the detection of nucleic acid sequences particular to the infectious organism. Depending on the nucleic acid sequence selected for detection, a diagnostic assay may be specific for an entire genus, more than one genus, a species or subspecies, auxotype, serovar (serotype), strain or other subset of organisms. This selectivity may be exploited in the development of simple reliable diagnostic tests for *C. trachomatis* and *N. gonorrhoeae* species of bacterial pathogens.

This background information is provided for the purpose of making known information believed by the applicant to be of possible relevance to the present invention. No admission is necessarily intended, nor should be construed, that any of the preceding information constitutes prior art against the present invention. Publications referred to throughout the specification are herein incorporated by reference in their entirety.

SUMMARY OF THE INVENTION

The present invention provides polynucleotide reagents useful for the detection of *Chlamydia trachomatis* and/or *Neisseria gonorrhoeae*. In particular, the present invention provides primers and probes for nucleic acid amplification and detection procedures, which specifically and sensitively detect various subspecies or serotypes and auxotypes of *C. trachomatis* and/or *N. gonorrhoeae*.

Two or more of the polynucleotide reagents provided herein as SEQ ID NOs: 1-12 can be combined in a composition, such as SEQ ID NO: 1 and one or more of SEQ ID NOs: 4-7 or such as SEQ ID NO: 2 and one or more of SEQ ID NOs: 4-7. Similarly, two more of the polynucleotide reagents provided herein can be combined such as one or more of SEQ ID NOs: 8 and one of SEQ ID NOs: 9-12, or SEQ ID NO: 9 and one of SEQ ID NOs: 8 and 10-12. In certain preferred embodiments, the above compositions comprise a first polynucleotide having a sequence selected from SEQ ID NOs: 1-3, a second polynucleotide having the sequence set forth in SEQ ID NO: 4, a third polynucleotide having the sequence set forth in SEQ ID NO: 8, and a fourth polynucleotide having the sequence set forth in SEQ ID NO: 9.

The primer sets herein provided comprise two primers, and are useful for the amplification of target sequences, e.g., in PCR. The primers designated SEQ ID NOs: 1-3 and SEQ ID NO: 4 specifically amplify *C. trachomatis*, and the primers designated SEQ ID NO: 8 and SEQ ID NO: 9 amplify serotypes and/or auxotypes of *N. gonorrhoeae*. The sequences identified herein as SEQ ID NOs: 5-7 are probe sequences useful for detecting amplified *Chlamydia trachomatis*, e.g., when *Chlamydia trachomatis* is amplified by primers having sequences identified by SEQ ID NOs: 1-3 and 4. Similarly, the sequences identified herein as SEQ ID NOs: 10-12 are useful for detecting amplified *N. gonorrhoeae*, e.g., when *N. gonorrhoeae* is amplified by primers having sequences identified by SEQ ID NOs: 8 and 9. Preferably, the primer and probe set comprises two primer sequences and one probe sequence. More preferably, the primer and probe set are used for PCR. Specific primer/probe sets that can be employed to amplify and detect *C. trachomatis* include primer/probe sets 1-9, which are set forth below. Similarly, specific primer/probe sets that can be employed to amplify and detect *N. gonorrhoeae* include primer/probe sets 10-12 which are set forth below.

The method for amplifying *C. trachomatis* and/or *N. gonorrhoeae* will generally comprise (a) forming a reaction mixture comprising nucleic acid amplification reagents, at least one polynucleotide of the invention, or composition, or primer set, or primer/probe set as mentioned above, and a test sample potentially containing at least one target sequence and (b) subjecting the mixture to amplification conditions to generate at least one copy of a nucleic acid sequence complementary to the target sequence.

The method for detecting *C. trachomatis* and/or *N. gonorrhoeae* will generally comprise (a) forming a reaction mixture comprising nucleic acid amplification reagents, at least one polynucleotide of the invention, or composition, or primer set, or primer/probe set as mentioned above, and a test sample potentially containing at least one target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of *C. trachomatis* and/or *N. gonorrhoeae* in the test sample.

Further, when the amplification is PCR, or a similar thermocycling amplification process, step (b) can be repeated multiple times to increase the number of target sequence copies. According to another embodiment, both *C. trachomatis* and *N. gonorrhoeae* can be detected in a single reaction mixture using a combination of the primer/probe sets, especially when a probe having SEQ ID NO: 5, 6, or 7 carries a label that produces a signal distinct from the signal generated by a probe having SEQ ID NO: 10, 11, or 12, and one of each set is contacted to a test sample amplified with SEQ ID NOs: 1-3 and 4, in combination with SEQ ID NOs: 8 and 9.

The polynucleotides of the present invention also can be provided as part of a kit useful for amplifying and for detecting *C. trachomatis* and/or *N. gonorrhoeae*. The kits comprise one or more suitable containers containing one or more primer sets or primer/probe sets or primer/probe combinations according to the present invention, an enzyme having polymerase activity and deoxynucleotide triphosphates. At least one sequence preferably bears a label.

In another aspect of the invention, a control target polynucleotide and a control polynucleotide probe are included in any of the methods or kits provided herein. In this aspect of the invention, the primer set preferably is complementary to the target sequence as well as the control target, whereas the target probe is preferably substantially complementary only to the target polynucleotide sequence and the control probe is preferably substantially complementary only to the control target.

Another aspect of the invention, provides isolated polynucleotides having a nucleotide sequence consisting essentially of, and preferably consisting of, the nucleotide sequences set forth in SEQ ID NOs: 2-12.

DETAILED DESCRIPTION OF THE INVENTION

The present invention provides polynucleotides that can specifically hybridise with a nucleic acid sequence, or complement thereof, of *Chlamydia trachomatis* (*C. trachomatis* or CT) and further provides other polynucleotides that can specifically hybridise with a nucleic acid sequence, or complement thereof, of *Neisseria gonorrhoeae* (*N. gonorrhoeae* or NG). These polynucleotides can be used to amplify *Chlamydia trachomatis* and *N. gonorrhoeae*, and to specifically detect the presence of each organism to the exclusion of the other. Presently, sixteen strains of *Chlamydia trachomatis* and 57 auxotypes and serovars of *N. gonorrhoeae* are known, and the method suitably and specifically detects all known strains.

The term "specifically hybridise" as used herein refers to the ability of a nucleic acid to bind detectably and specifically to a second nucleic acid. Polynucleotides specifically hybridise with target nucleic acid strands under hybridisation and wash conditions that minimise appreciable amounts of detectable binding to non-specific nucleic acids. Stringent conditions that can be used to achieve specific hybridisation are known in the art.

A "target sequence" or "target nucleic acid sequence" as used herein means a nucleic acid sequence of CT or NG, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded. In cases where the target is double stranded, polynucleotide primer sequences of the present invention preferably will amplify both strands of the target sequence. A target sequence may be selected that is more or less specific for a particular organism. For example, the target sequence may be specific to an entire genus, to more than one genus, to a species or subspecies, serogroup, auxotype, serotype, strain, isolate or other subset of organisms. The polynucleotide sequences of the present invention are selected for their ability to specifically hybridize with a range of subspecies, or serotypes or auxotypes, of CT and NG.

The term "test sample" as used herein, means a sample taken from an organism or biological fluid that is suspected of containing or potentially contains a CT or NG target sequence. The test sample can be taken from any biological source, such as for example, tissue, blood, saliva, sputa, mucus, sweat, urine, urethral swabs, cervical swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

A polynucleotide, in the context of the present invention, is a nucleic acid polymer of ribonucleic acid (RNA), deoxyribonucleic acid (DNA), modified RNA or DNA, or RNA or DNA mimetics (such as, without limitation PNAs), and derivatives thereof, and homologues thereof. Thus, polynucleotides include polymers composed of naturally occurring nucleobases, sugars and covalent internucleoside (backbone) linkages as well as polymers having non-naturally-occurring portions that function similarly. Such modified or substituted nucleic acid polymers are well known in the art and for the purposes of the present invention, are referred to as "analogues." For ease of preparation and familiarity to the skilled artisan, polynucleotides are preferably modified or unmodified polymers of deoxyribonucleic acid or ribonucleic acid.

Polynucleotide analogues that are useful in the present invention include polymers with modified backbones or non-natural internucleoside linkages. In accordance with the present invention, modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl internucleoside linkages, mixed heteroatom and alkyl or cycloalkyl internucleoside linkages, or one or more short chain heteroatomic or heterocyclic internucleoside linkages. An example of such a non-phosphorus containing backbone is a morpholino linkage (see, for example, U.S. Pat. Nos. 5,185,444, 5,034,506, and 5,142,047 all of which are herein incorporated by reference). As is known in the art, modified nucleic acid polymers (analogues) may contain one or more modified sugar moieties. For example, sugar moieties may be modified by substitution at the 2' position with a 2-methoxyethoxy (2-MOE) group (see, for example, Martin et al., (1995) *Helv. Chim. Acta*, 78:486-504).

The present invention also contemplates analogues that are RNA or DNA mimetics, in which both the sugar and the internucleoside linkage of the nucleotide units are replaced with novel groups. In these mimetics the base units are maintained for hybridisation with the target sequence. An example of such a mimetic, which has been shown to have excellent hybridisation properties, is a peptide nucleic acid (PNA) (Nielsen et al., (1991) *Science*, 254:1497-1500; International Patent Application WO 92/20702, herein incorporated by reference). In PNA compounds, the sugar-backbone of an oligonucleotide is replaced with an amide containing backbone, for example an aminoethylglycine backbone. The nucleobases are retained and are bound directly or indirectly to the aza-nitrogen atoms of the amide portion of the backbone.

Contemplated polynucleotides of the invention further include derivatives wherein the nucleic acid molecule has been covalently modified by substitution, chemical, enzymatic, or other appropriate means with a moiety other than a naturally occurring nucleotide, for example with a moiety that functions as a label, as described herein.

The present invention further encompasses homologues of the polynucleotides having nucleic acid sequences set forth in SEQ ID NOs: 1-12. Homologues are nucleic acids having at least one alteration in the primary sequence set forth in any one of SEQ ID NOs: 1-12, that does not destroy the ability of the polynucleotide to specifically hybridise with a target sequence, as described above. Accordingly, a primary sequence can be altered, for example, by the insertion, addition, deletion or substitution of one or more of the nucleotides of, for example, SEQ ID NOs: 1-12. Thus, homologues that are fragments of a sequence disclosed in SEQ ID NOs: 1-12 may have a consecutive sequence of at least about 7, 10, 13, 14, 15, 16, 17, 18, 19 20, 21, 22, 23 or more nucleotides of the nucleic acid sequences of SEQ ID NO: 1-12, and will retain the ability to specifically hybridise with a target sequence, as described above. Ordinarily, the homologues will have a nucleic acid sequence having at least about 50%, 60%, 70%, 80%, 85%, 90% or 95% nucleic acid sequence identity with a nucleic acid sequence set forth in SEQ ID NOs: 1-12. Identity with respect to such sequences is defined herein as the percentage of nucleotides in the candidate sequence that are identical with the known polynucleotides after aligning the sequences and introducing gaps, if necessary, to achieve the maximum percent identity. Terminal (5' or 3') or internal deletions, extensions or insertions into the nucleotide sequence shall not be construed as affecting identity.

The polynucleotides of the present invention thus comprise primers and probes that specifically hybridize to a target sequence of the invention, for example the nucleic acid molecules having any one of the nucleic acid sequences set forth in SEQ ID NOs: 1-12, including analogues and/or derivatives of said nucleic acid sequences, and homologues thereof, that can specifically hybridise with a target sequence of the invention. As described below, polynucleotides of the invention can be used as primers and/or probes to amplify or detect *Chlamydia trachomatis* or *N. gonorrhoeae*.

Such hybridizing polynucleotides, however, are defined further as being novel and non-obvious over any prior art polynucleotide including that which hybridizes under appropriate stringency conditions, a target sequence according to the present invention.

The polynucleotides according to the present invention can be prepared by conventional techniques well known to those skilled in the art. For example, the polynucleotides can be prepared using conventional solid-phase synthesis using commercially available equipment, such as that available from Applied Biosystems USA Inc. (Foster City, Calif.), DuPont, (Wilmington, Del.), or Milligen (Bedford, Mass.). Modified polynucleotides, such as phosphorothioates and alkylated derivatives, can also be readily prepared by similar methods known in the art. See, for example, U.S. Pat. Nos. 5,464,746; 5,424,414; and 4,948,882.

The polynucleotides according to the present invention can be employed directly as probes for the detection, or quantitation, or both, of CT and/or NG nucleic acids in a test sample. The test sample is contacted with at least one of the polynucleotides of the present invention under suitable hybridisation conditions and the hybridization between the target sequence and at least one of the polynucleotides is then detected by methods well-known in the art.

The polynucleotides of the present invention may incorporate one or more detectable labels. Detectable labels are molecules or moieties having a property or characteristic that can be detected directly or indirectly and are chosen such that the ability of the polynucleotide to hybridise with its target sequence is not adversely affected. Methods of labeling nucleic acid sequences are well known in the art (see, for example, Ausubel et al., (1997 & updates) *Current Protocols in Molecular Biology*, Wiley & Sons, New York).

Detection labels have the same definition as "labels" previously defined and "capture labels" are typically used to separate extension products, and probes associated with any such products, from other amplification reactants. Specific binding members (as previously defined) are well suited for this purpose. Also, probes used according to this method may be blocked at their 3' ends so that they are not extended under hybridization conditions. Methods for preventing extension of a probe are well known and are a matter of choice for one skilled in the art Typically, adding a phosphate group to the 3' end of the probe will suffice for purposes of blocking extension of the probe.

In cases where labels are employed to detect primer-amplified products, primer sequences optionally can be labeled with either a capture label or a detection label. The probe sequence is used to hybridize with the sequence generated by the primer sequence, and typically hybridizes with a sequence that does not include the primer sequence. Similarly to the primer sequence, the probe sequence can also labeled with either a capture label or a detection label with the caveat that when the primer is labeled with a capture label, the probe is labeled with a detection label, and vice versa. Upon formation of the copy sequence/probe hybrids, the differential labels (i.e., capture and detection labels) on the copy sequence and probe sequence can be used to separate and detect such hybrids. In one embodiment of the present invention, detection is performed according to the protocols used by the commercially available Abbott LCx® instrumentation (Abbott Laboratories; Abbott Park, Ill.).

The polynucleotides according to the present invention are also suitable for use as capture probes in sandwich-type assays. Capture probes and sandwich hybridisation assays are well known in the art. Briefly, the polynucleotide capture probe is attached to a solid support and brought into contact with a test sample under suitable hybridisation conditions such that a probe:target hybrid is formed between the capture probe and any target nucleic acid present in the test sample. After one or more appropriate washing steps, the probe:target hybrid is detected, usually by means of a second "disclosure" probe or by a specific antibody that recognises the hybrid molecule. The use of the CT and/or NG polynucleotides of the invention as a capture or a disclosure probe, or both, in such sandwich hybridisation assays is thus considered to be within the scope of the present invention.

The present invention also contemplates the use of the polynucleotides in modified nucleic acid hybridisation assays. For example, U.S. Pat. No. 5,627,030 discloses a method to amplify the detection signal in a nucleic acid hybridisation assay. In the disclosed assay, a first polynucleotide probe sequence is hybridised under suitable conditions to a target sequence, the probe:target hybrid is subsequently immunocaptured and immobilised. A second polynucleotide probe which contains many repeating sequence units is then hybridised to the probe component of the probe:target hybrid. Detection is achieved by hybridisation of many labeled nucleic acid sequence probes, one to each of the repeating sequence units present in the second probe. The attachment of multiple labeled probes to the second probe thus amplifies the detection signal and increases the sensitivity of the assay. The use of the polynucleotides of the instant invention in modified hybridisation assays of this type, either directly as a first probe, or as a second probe after modification to incorporate additional repeating sequence units by standard techniques, is thus considered to be within the scope of the present invention.

i) Amplification and Detection of CT and/or NG Nucleotide Sequences

The polynucleotides of the invention can be used as primers or probes to amplify and/or detect CT or NG in a test sample. The primer/probe sets provided herein comprise two primers and at least one probe. These primer/probe sets can be employed according to nucleic acid amplification techniques. Hence, the primers in any particular primer/probe set can be employed to amplify a target sequence. In most cases, the probe hybridizes to the copies of the target sequence generated by one of the primers and generally facilitates detecting any copies of the target sequence generated during the course of the amplification reaction. All of the primer/probe sets can be employed according to nucleic acid amplification procedures to specifically and sensitively detect either CT or NG, or both CT and NG when the appropriate primers and probes are combined. It is contemplated that the individual primers and probes of the primer/probe sets provided herein may alternatively be used in combination with primers and/or probes other than those described in the primer/probe sets provided herein.

Amplification procedures are well-known in the art and include, but are not limited to, polymerase chain reaction (PCR), TMA, rolling circle amplification, nucleic acid sequence based amplification (NASBA), and strand displacement amplification (SDA). One skilled in the art will understand that for use in certain amplification techniques the primers may need to be modified, for example, for SDA the primer comprises additional nucleotides near its 5' end that constitute a recognition site for a restriction endonuclease. Similarly, for NASBA the primer comprises additional nucleotides near the 5' end that constitute an RNA polymerase promoter. Polynucleotides thus modified are considered to be within the scope of the present invention.

As is well known in the art, certain criteria need to be taken into consideration when selecting a primer for an amplification reaction. For example, when a primer pair is required for the amplification reaction, the primers should be selected such that the likelihood of forming 3' duplexes is minimised, and such that the melting temperatures ($T_M$) are sufficiently similar to optimise annealing to the target sequence and minimise the amount of non-specific annealing. In this context, the polynucleotides according to the present invention are provided in combinations that can be used as primers in amplification reactions to specifically amplify target nucleic acid sequences.

In one embodiment of the present invention, therefore, polynucleotides having the nucleic acid sequences as set forth in SEQ ID NOs: 1, 2, or 3 used in combination with the nucleic acid sequences as set forth in SEQ ID NO: 4, which are provided with polynucleotides having the nucleic acid sequences as set forth in SEQ ID NOs: 8 and 9. In a related embodiment, these primer combinations are used to specifically amplify CT and/or NG nucleic acid sequences, if present in a test sample. Primers included in the primer/probe sets 1-9 (further defined below) can be used to prime synthesis and amplification of copies of a CT target sequence in the case of SEQ ID NOs: 1, 2, or 3 and 4; and copies of a NG target sequence in the case of primer/probe sets 10-12 and SEQ ID NOs: 8 and 9. The remaining SEQ ID NOs (SEQ ID NOs: 5-7 and 10-12) can specifically hybridize with the amplification products of the primer sequences found in the same primer/probe set. For example, primer/probe set 10 is specific for NG insofar as SEQ ID NOs: 8 and 9 prime synthesis of the NG target sequence and SEQ ID NO: 10 hybridizes with the amplification products produced by SEQ ID NOs: 8 and 9.

The amplification method of the present invention generally comprises (a) forming a reaction mixture comprising nucleic acid amplification reagents, at least one primer/probe set of the present invention, and a test sample suspected of containing a at least one target sequence and (b) subjecting the mixture to amplification conditions to generate at least one copy of a nucleic acid sequence complementary to the target sequence.

Step (b) of the above methods can be repeated any suitable number of times (prior to step (c) in the detection method), e.g., by thermal cycling the reaction mixture between 10 and 100 times, typically between about 20 and about 60 times, more typically between about 25 and about 45 times.

Nucleic acid amplification reagents include reagents which are well known and may include, but are not limited to, an enzyme having at least polymerase activity, enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

Amplification conditions are conditions that generally promote annealing and extension of one or more nucleic acid sequences. It is well known that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures that are about 10° C. (e.g., 2° C. to 18° C.) below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer/probe set is well within ordinary skill of one practicing this art.

As mentioned earlier, the primer sequences (SEQ ID NOs: 1-4, 8 and 9) of any particular primer/probe set can, by themselves or with additional polynucleotides, be used as amplification primers according to nucleic acid amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930. Each of these exemplary amplification reactions generate multiple copies of a DNA target sequence.

In one embodiment of the present invention, the detection method generally comprises (a) forming a reaction mixture comprising nucleic acid amplification reagents, at least one primer/probe set of the present invention, and a test sample suspected of containing at least one target sequence; (b) subjecting the mixture to amplification conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of the target sequence (CT and/or NG and/or a control sequence) in the sample.

Specific amplicons produced by amplification of target nucleic acid sequences using the polynucleotides of the present invention, as described above, can be detected by a variety of methods known in the art. For example, one or more of the primers used in the amplification reactions may be labeled such that an amplicon can be directly detected by conventional techniques subsequent to the amplification reaction. Alternatively, a probe consisting of a labeled version of one of the primers used in the amplification reaction, or a third polynucleotide distinct from the primer sequences that has been labeled and is complementary to a region of the amplified sequence, can be added after the amplification reaction is complete. The mixture is then submitted to appropriate hybridisation and wash conditions and the label is detected by conventional methods.

The amplification product produced as above can be detected during or subsequently to the amplification of the target sequence. Methods for detecting the amplification of a target sequence during amplification are outlined above, and described, for example, in U.S. Pat. No. 5,210,015. Gel electrophoresis can be employed to detect the products of an amplification reaction after its completion. Alternatively, amplification products are hybridized to probes, then separated from other reaction components and detected using microparticles and labeled probes.

It will be readily appreciated that a procedure that allows both amplification and detection of target nucleic acid sequences to take place concurrently in a single unopened reaction vessel would be advantageous. Such a procedure would avoid the risk of "carry-over" contamination in the post-amplification processing steps, and would also facilitate high-throughput screening or assays and the adaptation of the procedure to automation. Furthermore, this type of procedure allows "real-time" monitoring of the amplification reaction as well as more conventional "end-point" monitoring.

The present invention thus includes the use of the polynucleotides in a method to specifically amplify and detect target nucleic acid sequences in a test sample in a single tube format. This may be achieved, for example, by including in the reaction vessel an intercalating dye such as SYBR Green or an antibody that specifically detects the amplified nucleic acid sequence. Alternatively a third polynucleotide distinct from the primer sequences, which is complementary to a region of the amplified sequence, may be included in the reaction, as when a primer/probe set of the invention is used.

For use in an assay as described above, in which both amplification with polynucleotide primers and detection of target sequences using a polynucleotide probe occur concurrently in a single unopened reaction vessel, the polynucleotide probe needs to possess certain properties. For example, since the probe will be present during the amplification reaction, it should not interfere with the progress of this reaction and should also be stable under the reaction conditions. In addition, for real-time monitoring of reactions, the probe should be capable of binding its target sequence under the conditions of the amplification reaction and to emit a signal only upon binding this target sequence. Examples of probe molecules that are particularly well-suited to this type of procedure include molecular beacon probes and TaqMan® probes.

The present invention, therefore, contemplates the use of the polynucleotides as TaqMan® probes. As is known in the art, TaqMan® probes are dual-labeled fluorogenic nucleic acid probes composed of a polynucleotide complementary to the target sequence that is labeled at the 5' terminus with a fluorophore and at the 3' terminus with a quencher. TaqMan® probes are typically used as real-time probes in amplification reactions. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and thus produces a detectable signal.

The present invention further contemplates the use of the polynucleotides as "molecular beacon" probes. Molecular beacon probes are well known in the art, for example, see U.S. Pat. Nos: 6,150,097; 5,925,517 and 6,103,476. Basically, molecular beacons are polynucleotide probes capable of forming a stem-loop (hairpin) structure. The loop is a single-stranded structure containing sequences complementary to the target sequence, whereas the stem typically is unrelated to the target sequence and self-hybridises to form a double-stranded region. Nucleotides that are both complementary to the target sequence and that can self-hybridise may also form part of the stem region. Attached to one arm of the stem is a fluorophore moiety and to the other arm a quencher moiety. When the polynucleotide adopts a hairpin shape, the fluorophore and the quencher are in close proximity and the energy emitted by the fluorophore is thus absorbed by the quencher and given off as heat, resulting in internal quenching of the fluorophore. Upon binding of the polynucleotide to its target sequence, the fluorophore and the quencher become spatially separated and the fluorophore can fluoresce producing a detectable signal. Preferably, the primers and probes of the present invention are selected such that the probe stably (e.g., less than 5% of probe bound to amplicon is displaced over 24 hours under the hybridization conditions for the probe to the amplicon) binds to the amplicon when the reaction is cooled from a denaturation temperature, e.g., 90° C. to 96° C., to a temperature below the Tm for the binding of the probe with the amplicon.

The present invention further contemplates the use of polynucleotides of the invention as linear probes in conjunction with a fluorophore and a high efficiency quencher, such as the Black Hole Quenchers (BHQ™; Biosearch Technologies, Inc., Novato, Calif.). As is known in the art, the high quenching efficiency and lack of native fluorescence of the BHQ™ dyes allows "random-coil" quenching to occur in linear probes labeled at one terminus with a fluorophore and at the other with a BHQ™ dye thus ensuring that the fluorophore does not fluoresce when the probe is in solution. Upon binding its target sequence, the probe stretches out, the fluorophore and quencher are thus spatially separated and the fluorophore fluoresces. One skilled in the art will appreciate that the BHQ™ dyes can also be used as the quencher moiety in molecular beacon or TaqMan™ probes.

Suitable fluorophores and quenchers for use with the polynucleotides of the present invention can be readily determined by one skilled in the art (see also, Tyagi et al., *Nature Biotechnol.*, 16:49-53 (1998); Marras et al., *Genet. Anal.: Biomolec. Eng.*, 14:151-156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives such as a dihalo-($C_1$ to $C_8$)dialkoxycarboxyfluorescein, 5-(2'-aminoethyl)aminonaphthalene-1-sulphonic acid (EDANS), coumarin and coumarin derivatives, Lucifer yellow, Texas red, tetramethylrhodamine, tetrachloro-6-carboxyfluoroscein, 5-carboxyrhodamine, cyanine dyes and the like. Quenchers include, but are not limited to, DABCYL, 4'-(4-dimethylaminophenylazo)benzoic acid (DABSYL), 4-dimethylaminophenylazophenyl-4'-maleimide (DABMI), tetramethylrhodamine, carboxytetramethylrhodamine (TAMRA), BHQ™ dyes and the like. Methods of coupling fluorophores and quenchers to nucleic acids are well known in the art.

In one embodiment of the present invention, the probes are molecular beacon probes. As is known in the art, certain criteria need to be met for a molecular beacon probe to be successful in monitoring or detecting an amplification reaction. The present invention, therefore, provides molecular beacon probes that comprise polynucleotides of the present invention together with flanking self-complementary regions. The polynucleotides of the present invention may make up the loop region of the molecular beacon, or they may make up the loop region and part of the stem region. Thus, the self-complementary stem sequences can be unrelated to the target sequence or may contain one or more nucleotides that are complementary to the target sequence.

In one embodiment of the present invention, polynucleotides having a nucleic acid sequence as set forth in any one of SEQ ID NOs: 7 or 12, or homologues of these polynucleotides, together with appropriate self-complementary flanking sequences are provided as molecular beacon probes. In a related embodiment, the molecular beacon probes have a nucleic acid sequence as set forth in any one of SEQ ID NOs: 7 or 12.

One skilled in the art will understand that the selection of primers to be used with the molecular beacon probe also requires certain criteria to be met. For example, it is important that there are no areas of complementarity that may cause the molecular beacon to bind to a primer, which would result in a high background signal.

The polynucleotides according to the present invention, therefore, are further provided in combinations, comprising two primers and at least one probe, that can be used to specifically amplify and detect target nucleic acid sequences in a test sample. In a related embodiment, primer/probe sets are provided for the amplification and detection of target nucleic acid sequences by molecular beacon PCR.

As is known in the art, molecular beacon probes can be used to monitor the progress of an amplification reaction in real time. During the course of an amplification reaction, such as a PCR, the molecular beacon interacts with its target sequence at the annealing temperature for the probe, and a fluorescent signal is generated. As the number of target strands produced in the amplification reaction increases, the number of molecular beacons bound to their target increases concomitantly, as does the strength of the fluorescent signal.

In accordance with the present invention, therefore, the combinations of two primers and at least one probe, as described above, can be used in either end-point amplification and detection assays, in which the strength of the detectable signal is measured at the conclusion of the amplification reaction, or in real-time amplification and detection assays, in which the strength of the detectable signal is monitored throughout the course of the amplification reaction.

Patients potentially infected with *N. gonorrhoeae* are often also at risk for infection with *Chlamydia trachomatis*. CT primers may be used in conjunction with primers for the amplification of NG to amplify target sequences from either or both organisms in a single amplification reaction. The co-amplification reaction, followed by species-specific hybridization reactions, allow for concurrent assessment of a test sample for infection with either CT, or NG, or both organisms. According to another embodiment of the invention, both CT and NG can be amplified and/or detected simultaneously in a single reaction mixture using a combination of two primer/probe sets (i.e. one selected from the CT specific primer/probe sets and the other selected from the NG specific primer/probe sets). For example, a test sample could be contacted with primer/probe sets 7 and 12, or with primer/probe sets 2 and 10, along with amplification reagents to amplify and detect the presence of CT and NG in a test sample. It is understood by one skilled in the art that when two or more distinct target sequences are to be detected in the same reaction mixture, each probe must be detectably distinct from each of the other probes. For example if two or more molecular beacon probes are present in the same reaction mixture, the fluorophore moieties of each beacon probe should fluoresce at different wavelengths.

The polynucleotides according to the present invention can also be used in assays to quantitate the amount of CT and/or NG nucleic acid present in a sample. Thus, the polynucleotides according to the present invention can be used in a method to specifically amplify, detect and quantitate target nucleic acid sequences in a test sample, which generally comprises the steps of:
(a) forming a reaction mixture comprising nucleic acid amplification reagents, at least one polynucleotide probe sequence that incorporates a label which produces a detectable signal upon hybridisation of the probe to its target sequence, at least one polynucleotide primer and a test sample that contains one or more target nucleic acid sequences;
(b) subjecting the mixture to amplification conditions to generate at least one copy of the target nucleic acid sequence, or a nucleic acid sequence complementary to the target sequence;
(c) hybridising the probe to the target nucleic acid sequence or the nucleic acid sequence complementary to the target sequence, so as to form a probe:target hybrid;
(d) detecting the probe:target hybrid by detecting the signal produced by the hybridised labeled probe; and
(e) comparing the amount of the signal produced to a standard as an indication of the amount of target nucleic acid sequence present in the test sample.

One skilled in the art will understand that, as outlined above, step (b) of the above method can be repeated several times prior to step (c) by thermal cycling the reaction mixture by standard techniques known in the art.

Various types of standards for quantitative assays are known in the art. For example, the standard can consist of a standard curve compiled by amplification and detection of known quantities of CT or NG nucleic acids under the assay conditions. Alternatively, an internal standard can be included in the reaction. Such internal standards generally comprise a control target nucleic acid sequence and a control polynucleotide probe. The internal standard can optionally further include an additional pair of primers. The primary sequence of these control primers may be unrelated to the polynucleotides of the present invention and specific for the control target nucleic acid sequence. Alternatively, no additional primer need be used if the control target sequence is designed such that it binds at one end with a primer from a first primer/probe set directed to a first target sequence (for example, CT), and binds at the other end with a primer for a second primer/probe set directed to a second target sequence (for example, NG), such that copies will be generated under amplifying conditions.

In the context of the present invention, a control target nucleic acid sequence is a nucleic acid sequence that:
(a) can be amplified either by a CT or NG primer or primer pair being used in a particular reaction or by distinct control primers;
(b) specifically hybridises to the control probe under suitable conditions; and
(c) does not hybridise with a CT- or NG-specific probe under the same conditions.

In the context of the present invention, in addition to fulfilling the standard requirements for probe molecules, the control polynucleotide probe for use in quantitation reactions:
(a) specifically hybridises to the control sequence under suitable conditions;
(b) does not hybridise with a CT sequence, to the CT-specific probe, or to the CT-specific primers under the same conditions, when a CT target sequence is being detected;
(c) does not hybridise with a NG sequence, to the NG-specific probe, or to the NG-specific primers under the same conditions, when a NG target sequence is being detected;
(d) incorporates a detectable label that is distinct from the label incorporated into other probes (for example CT and/or NG probes) in use in the same reaction mixture. The signals generated by these various labels when they bind their respective target sequences can thus be distinguished and quantified separately.

One skilled in the art will recognise that the actual nucleic acid sequence of the control target nucleic acid and the control probe is not important provided that they both meet the criteria outlined above.

In the context of the present invention, the amount of target nucleic acid in a test sample can be quantified using "end point" methods or "real time" methods. One skilled in the art will appreciate that when used as CT- or NG-specific probes in quantitative assays, the polynucleotides of the present invention can be conventional hybridisation probes, linear BHQ™ probes, TaqMan® probes, molecular beacon probes, or combinations or modified versions thereof. In one embodiment of the present invention, the polynucleotides are used as molecular beacon probes.

The present invention also contemplates the provision of any one or more of the polynucleotides of the invention, for example any one of the primer sets or primer/probe sets of the invention together with a control target nucleic acid sequence, which can be amplified by the specified primer pair, and a control polynucleotide probe for the quantitative reactions. The present invention further provides for the inclusion of control primers, which specifically amplify the control target nucleic acid sequence, in the quantitative reactions.

The amplification and/or detection methods in which the polynucleotides according to the present invention can be employed are suitable for adaptation as high-throughput assays. High-throughput assays provide the advantage of processing many samples simultaneously and significantly decrease the time required to screen a large number of samples. The present invention, therefore, contemplates the use of the polynucleotides of the present invention in high-throughput screening or assays to detect and/or quantitate CT and/or NG nucleic acids in a plurality of test samples.

For high-throughput assays, reaction components are usually housed in a multi-container carrier or platform, such as a multi-well microtiter plate, which allows a plurality of assay reactions containing different test samples to be monitored in the same assay. The present invention also contemplates highly automated high-throughput assays to increase the efficiency of the screening or assay process. Many high-throughput screening or assay systems are now available commercially, as are automation capabilities for many procedures such as sample and reagent pipetting, liquid dispensing, timed incubations, formatting samples into microarrays, microplate thermocycling and microplate readings in an appropriate detector, resulting in much faster throughput times.

The polynucleotides in accordance with the present invention can be provided as part of a kit that allows for the detection and/or quantitation of CT and/or NG nucleic acids. Such kits comprise one or more of the polynucleotides of the invention for use as a primer and/or probe. In one embodiment of the present invention, the polynucleotides are provided in the kits in combinations for use as primers to specifically amplify CT and/or NG nucleic acids in a test sample. In a related embodiment, the polynucleotides are provided in combinations that comprise the nucleic acid sequences as set forth in SEQ ID NOs: 1 and 4; and/or SEQ ID NOs: 8 and 9.

In another embodiment, the polynucleotides are provided in the kits in combinations comprising at least two primers and at least one probe. In a related embodiment, the polynucleotides are provided in combinations that comprise the nucleic acid sequences as set forth in SEQ ID NOs: 1, 4, and 5; SEQ ID NOs: 2, 4, and 5; SEQ ID NOs: 3, 4, and 5, SEQ ID NOs: 1, 4, and 6; SEQ ID NOs: 2, 4, and 6; SEQ ID NOs: 8, 9 and 10; SEQ ID NOs: 8, 9 and 11; or SEQ ID NOs: 8, 9 and 12. Kits comprising combinations of more than one primer/probe set are also envisaged, e.g., without limitation, SEQ ID NOs: 1, 4, 5, 8, 9 and 10; and SEQ ID NOs: 2, 4, 5, 8, 9 and 10.

Kits for the detection of CT and/or NG nucleic acids may additionally contain a control target nucleic acid and a control polynucleotide probe. Thus, in one embodiment of the present invention, the kits comprise one of the above combinations of polynucleotides comprising at least two primers and at least one probe, together with a control target nucleic acid sequence, which can be amplified by the specified primer pair, and a control polynucleotide probe. The present invention further provides kits that include control primers, which specifically amplify the control target nucleic acid sequence.

The kits can optionally include amplification reagents, reaction components and/or reaction vessels. Typically, at least one sequence bears a label, but detection is possible without this. Thus, one or more of the polynucleotides provided in the kit may have a detectable label incorporated, or the kit may include reagents for labeling the polynucleotides. One or more of the components of the kit may be lyophilised and the kit may further comprise reagents suitable for the reconstitution of the lyophilised components. The kit can additionally contain instructions for use.

The polynucleotides, methods, and kits of the present invention are useful in clinical or research settings for the detection and/or quantitation of CT and/or NG nucleic acids. Thus, in these settings the polynucleotides can be used in assays to diagnose CT and/or NG infection in a subject, or to monitor the quantity of a CT and/or NG target nucleic acid sequence in a subject infected with CT and/or NG. Monitoring the quantity of bacteria in a subject is particularly important in identifying or monitoring response to anti-bacterial therapy.

Primers and probes useful for amplifying and/or detecting *Chlamydia trachomatis* (CT) or *Neisseria gonorrhoeae* (NG) are presented below in Table 1.

TABLE 1

| Polynucleotide | Sequence (5'-3') | SEQ ID NO |
|---|---|---|
| CT Forward primer | GGGATTCCTG TAACAACAAG TCAGG | 1 |
| Alternative CT Forward primer | GGGATTCDTG TAACAACAAG TCAGG (wherein D is not C) | 2 |
| Preferred embodiment of SEQ ID NO: 2 | GGGATTCGTG TACAACAAG TCAGG, | 3 |
| CT Reverse primer | GCTTGCACGA AGTACTCTAG GAG | 4 |
| CT Probe | ATAGCACTAT AGAACTCTGC AA | 5 |
| Alternative CT Probe | CATAGCACTA TAGAACTCTG CAAGCC | 6 |
| CT Beacon probe | ctggcATAGC ACTATAGAAC TCTGCAAgcc ag | 7 |
| NG Forward primer | CGACGTACCG GTTTTTGTTC | 8 |
| NG Reverse primer | CGGCTCCTTA TTCGGTTTGA CC | 9 |
| NG Probe | ACACCGCCCG GAACCCGA | 10 |
| Alternative NG Probe | GAAACACCGC CCGGAACCCG AT | 11 |
| NG Beacon probe | ctcggACACC GCCCGGAACC CGAg | 12 |

In Table 1, polynucleotide probe sequences complementary to the bacterial sequences are indicated in capital letters; lower case nucleotides are self-complementary so as to form a stem of a beacon probe under suitable conditions; and in some instances, nucleotides complementary to the bacterial sequences also form part of the self-complementary beacon probe stem.

The nucleic acids having polynucleotide sequences of Table 1 can be combined in suitable combinations to form a primer/probe set useful in the context of the present invention. Suitable primer probe sets include, but are not limited to:
Primer and Probe Set 1: SEQ ID NOs: 1, 4, and 5;
Primer and Probe Set 2: SEQ ID NOs: 2, 4, and 5;
Primer and Probe Set 3: SEQ ID NOs: 3, 4, and 5;
Primer and Probe Set 4: SEQ ID NOs: 1, 4, and 6;
Primer and Probe Set 5: SEQ ID NOs: 2, 4, and 6;
Primer and Probe Set 6: SEQ ID NOs: 3, 4, and 6;
Primer and Probe Set 7: SEQ ID NOs: 1, 4, and 7;
Primer and Probe Set 8: SEQ ID NOs: 2, 4, and 7;
Primer and Probe Set 9: SEQ ID NOs: 3, 4, and 7;
Primer and Probe Set 10: SEQ ID NOs: 8, 9, and 10;
Primer and Probe Set 11: SEQ ID NOs: 8, 9, and 11; and
Primer and Probe Set 12: SEQ ID NOs: 8, 9, and 12.

The following examples are for illustrative purposes only and should not be construed to limit the scope of this invention in any way.

EXAMPLES

The following examples demonstrate detection of various subtypes of CT and NG using the primer/probe sets described above. These DNA primers and probes comprising the primer/probe sets are identified as SEQ ID NOs: 1-7 are specific for CT, and SEQ ID NOs: 8-12 are specific for NG.

In the following examples, SEQ ID NOs: 1 and 4 are used as consensus amplification primers specific for the CT target sequence. SEQ ID NO: 6 or 7 is used as consensus internal hybridization probes for the CT amplification product. SEQ ID NOs: 8 and 9 are used as consensus amplification primers specific for the NG target sequence and SEQ ID NO: 10 or 12 is used as consensus internal hybridization probes for the NG amplification product.

Example 1

Preparation of Primers and Probes

A. CT and NG Consensus Primers

Consensus primers were designed to detect all known CT or NG subtypes by oligonucleotide hybridization PCR. In the following examples, these primers were SEQ ID NO: 1 and SEQ ID NO: 4 for CT, and SEQ ID NO: 8 and SEQ ID NO: 9 for NG. SEQ ID NO: 3 was found to have some advantages relative to SEQ ID NO: 1 for some embodiments of the present invention, which relate to ease of purification of these polynucleotides. However, those embodiments are not illustrated below, and the inventors prefer use of SEQ ID NO: 1 to use of SEQ ID NO: 3.

B. CT and NG Consensus Probes

Consensus probes were designed to hybridize with the amplified CT or NG target sequence by oligonucleotide hybridization. These probe sequences were modified for use as probes in a molecular beacon assay by the addition of terminal nucleotides to generate self-complementary 5' and 3' ends, and of fluorescent (fluo) and quenching moieties at opposite ends of the polynucleotide (see Table 2). Thus the CT probe sequence of SEQ ID NO: 6 was the basis of the molecular beacon probe of SEQ ID NO: 7, and the NG probe sequence of SEQ ID NO: 10 was the basis of the molecular beacon probe of SEQ ID NO: 12. Where more than one beacon probe was used simultaneously in the same molecular beacon assay, fluorescing moieties with different excitation-emission profiles were used to distinguish between the different probe signals.

Probe sequences were synthesized using standard oligonucleotide synthesis methodology.

TABLE 2

| | Sequence (5'-3') |
|---|---|
| CT beacon probe | Fluor-ctggcATAGC ACTATAGAAC TCTGCAAgcc ag-quencher (SEQ ID NO: 7) |
| NG beacon probe | Fluor-ctcggACACC GCCCGGAACC CGAg-quencher (SEQ ID NO: 12) |

Example 2

Preparation of Sample DNA

CT DNA was isolated from CT serotype Ba, Apache-2 strain (ATCC VR-347. Rockville, Md.) using methods known in the art, and used to assess the sensitivity, specificity and cross-reactivity of the CT consensus primer/probe sets. NG DNA was similarly prepared and used to assess the sensitivity, specificity and cross-reactivity of the CT consensus primer/probe sets.

In negative control samples ("Neg"), an equal volume of diluent was substituted for sample DNA. Various concentrations of sample DNA of a known concentration were included as positive control ("0.12×", "1×", "10×").

An internal control (IC) target polynucleotide was designed as positive control for amplification, for use with CT and NG primers. The sequence targeted for amplification was complementary to a CT primer at one end and a NG primer at the other end, such that in the presence of both primers the control sequence would be amplified under amplifying conditions. The polynucleotide was designed to yield an amplicon complementary to a control probe, for example a molecular beacon probe, but not complementary to the probes in use for the detection of either CT or NG. This control target polynucleotide was prepared using methods well known in the art.

Example 3

Sensitivity of CT Detection

CT DNA was prepared as described in Example 2. Primer/probe set 7 was evaluated (i.e., SEQ ID NOs: 1 and 4 were used as primers and SEQ ID NO: 7 as the probe). All sequences were prepared as described in Example 1.

Dilutions of the isolated CT DNA were PCR amplified and detected using primer/probe set 7. PCR was performed in 1× GeneAmp® PCR Gold Buffer, 0.25 mM EDTA and 0.125 mM EGTA. Amplitaq Gold™ DNA polymerase was used at a concentration of 10 units/reaction, with dNTPs (dATP, dGTP, dTTP and dCTP) present at a final concentration of 0.20 mM each. A final concentration of 8 mM $MgCl_2$ was used in a total reaction volume of 0.1 ml. Sample volumes were 50 containing none or $10'$-$10^6$ Chlamydial elementary bodies (EB)/reaction. Primers were used at a concentration of 200-400 nM each, and beacon probes at a concentration of 100 nM each. An internal control (IC) target sequence and control probe were present at a final concentration of 500 copies/reaction and 100 nM respectively.

Reaction mixtures were amplified in a Perkin-Elmer Thermal Cycler. Reaction mixtures were first incubated at 95° C. for 9.5 minutes. PCR amplification was then accomplished in 45 cycles with each cycle being 95° C. for 30 seconds then 59° C. for 60 seconds. After the reaction mixtures were thermal cycled, the mixtures were maintained at 95° C. for 3 minutes and then lowered to 25° C. for 10 minutes for probe hybridization. Reaction products were detected on a robotic microplate fluorescence reader using the following emission maxima and band widths (in nm):

TABLE 3

|  | $1^{st}$ Fluor | 2d Fluor | 3d Fluor |
| --- | --- | --- | --- |
| Excitation | 485/20 | 534/8 | 585/8 |
| Emission | 517/8 | 562/12 | 612/12 |

Data from this experiment is presented in TABLE 4 and shows detection of CT serotype Ba at concentrations as low as 10 EB/reaction using primer/probe set 3.

TABLE 4

| [CT] (EB/reaction) | Measured Fluorescence |
| --- | --- |
| 0 | 2559 |
| 10 | 10441 |
| 100 | 12451 |
| 1000 | 12760 |
| 10,000 | 14819 |
| 1,000,000 | 17243 |

Thus, this Example shows good target response over a range of 10 to $10^6$ EB/reaction.

Example 4

Cross-Reactivity Between CT and NG

To test for cross-reactions between CT and NG primer/probe sets, target DNA and primer/probe sets for both CT and NG were combined in each reaction mixture to simultaneously detect CT and NG DNA in test samples. CT and NG DNA were prepared as in Example 2, and the samples prepared as outlined below. The CT primer/probe set #7 (SEQ ID NOs: 1 and 4 as primers and SEQ ID NO: 7 as probe) and NG primer/probe set #12 (SEQ ID NOs: 8 and 9 as primers and SEQ ID NO: 12 as probe) were prepared as described in Example 1 and used either together or separately to amplify and detect the dilutions of CT and NG DNA.

The samples included 2 cross-reactivity panels (samples 1-58 and samples 1B-23B) as well as negative (Neg) and positive controls (0.12×, 1× and 10×). Each reaction mixture comprised a final concentration of 0.40 uM CT forward primer (SEQ ID NO: 1), 0.20 uM CT reverse primer (SEQ ID NO: 4), 0.10 uM CT beacon probe (SEQ ID NO: 7), 0.20 uM NG forward primer (SEQ ID NO: 8), 0.20 uM NG reverse primer (SEQ ID NO: 9), 0.10 uM NG beacon probe (SEQ ID NO: 12), 5 units of Amplitaq DNA Polymerase, 1 mM dNTPs, and 8 mM $MgCl_2$ in 1×PCR Buffer II. 100 ul reactions were cycled 45 times through 95° C./30 sec and 59° C./1 min for DNA amplification, followed by 1 cycle at 95° C./3 mM and 25° C./10 min for final denaturation and probe annealing.

Importantly, detection of CT was not altered by the inclusion of the NG primer/probe set with the CT primer/probe set in the CT reaction mixtures, with sensitivity remaining at approximately 10' organisms per reaction. Similarly, detection of NG was not altered by the inclusion of the CT primer/probe set with the NG primer/probe set in the NG reaction mixtures, with sensitivity remaining at approximately 10' organisms per reaction.

The NG assay reagents detected NG, but did not detect any of over 50 other non-sexually transmitted (non-STD) strains of *Neisseria*, nor 3 strains of *Chlamydia* (*trachomatis, pneumoniae*, and *psittaci*).

Example 5

CT Serovar Detection

To determine whether and with what sensitivity primers and probes of the invention could detect a range of CT serovars, a dilution panel of 15 CT serotypes was tested in reactions that included primer/probe sets for both CT and NG, and suitable negative (Neg) and positive (1× and 0.12×) control samples. The CT primer/probe set #7 and NG primer/probe set #12 were prepared as described in Example 1, and the CT and NG control DNA were prepared as in Example 2.

The CT serovar samples were present in the reaction mixtures at final concentrations in the range of 10-1000 molecules per reaction. Each reaction mixture comprised a final concentration of 0.40 uM CT forward primer (SEQ ID NO: 1), 0.20 uM CT reverse primer (SEQ ID NO: 4), 0.10 uM CT beacon probe (SEQ ID NO: 7), 0.45 uM NG forward primer (SEQ ID NO: 8), 0.25 uM NG reverse primer (SEQ ID NO: 9), 0.10 uM NG beacon probe (SEQ ID NO: 12), 3 units of Amplitaq DNA Polymerase, 1 mM dNTPs, and 8 mM $MgCl_2$ in 1×PCR Buffer II. 100 ul reactions were cycled 45 times through 95° C./30 sec and 59° C./1 min for DNA amplification, followed by 1 cycle at 95° C./3 mM and 25° C./10 min for final denaturation and probe annealing.

Sixteen serovars of *Chlamydia trachomatis* were detected using primer/probe sets of the present invention over concentrations of 10-1000 copies per reaction.

Example 6

NG Auxotype Detection

To determine whether and with what sensitivity primers and probes of the invention could detect a range of NG subtypes, a dilution panel of 7 NG auxotypes was tested in reactions that included primer/probe sets for both CT and NG, and suitable negative (Neg) and positive (1× and 0.12×) control samples. The CT primer/probe set #7 and NG primer/probe set #12 were prepared as described in Example 1, and the CT and NG control DNA were prepared as in Example 2.

The NG auxotype samples were present in the reaction mixtures at final concentrations in the range of 10-1000 molecules per reaction. Each reaction mixture comprised a final concentration of 0.40 uM CT forward primer (SEQ Ill NO: 1), 0.20 uM CT reverse primer (SEQ ID NO: 4), 0.10 uM CT beacon probe (SEQ ID NO: 7), 0.20 uM NG forward primer (SEQ ID NO: 8), 0.20 uM NG reverse primer (SEQ ID NO: 9), 0.10 uM NG beacon probe (SEQ ID NO: 12), 3 units of Amplitaq DNA Polymerase, 1 mM dNTPs, and 8 mM $MgCl_2$ in 1×PCR Buffer II. Reactions were cycled 45 times through 95° C./30 sec and 59° C./1 min for DNA amplification, followed by 1 cycle at 95° C./3 min and 25° C./10 mM for final denaturation and probe annealing.

Six auxotypes of NG were tested, and all tested auxotypes were detected with high sensitivity (10 copies per reaction) using the primer/probe sets of the invention. In addition, no cross reactivity was observed with the CT primer set even when NG was present at a high concentration ($10^7$ NG molecules per reaction).

All publications, references, patents and patent applications referred to above are specifically incorporated by reference to the same extent as if each reference were individually incorporated by reference in its entirety While the invention has been described in detail and with reference to specific embodiments, it will be apparent to one skilled in the art that various changes and modifications may be made to such embodiments without departing from the spirit and scope of the invention.

What is claimed is:

1. A composition comprising three polynucleotides consisting of SEQ ID NO: 8, SEQ ID NO: 9, and SEQ ID NO: 12, wherein the polynucleotide of SEQ ID NO: 12 is labeled with a detectable label.

2. A primer/probe set consisting of polynucleotides of SEQ ID NOs: 8, 9, and 12, wherein the polynucleotide of SEQ ID NO: 12 is labeled with a detectable label.

3. A method of amplifying *Neisseria gonorrhoeae* in a test sample, said method comprising:
 (a) forming a reaction mixture comprising nucleic acid amplification reagents, a test sample potentially containing a *Neisseria gonorrhoeae* target sequence a composition according to claim 1; and
 (b) subjecting the mixture to amplification conditions to generate at least one copy of a nucleic acid sequence complementary to the target sequence.

4. The method of claim 3 wherein the amplification conditions include changing the temperature of the sample and the temperature change is repeated between 10 and 100 times.

5. A method of detecting *Neisseria gonorrhoeae* in a test sample, said method comprising:
 (a) forming a reaction mixture comprising nucleic acid amplification reagents, a test sample potentially containing a *Neisseria gonorrhoeae* target sequence, and
 (b) subjecting the mixture to amplification conditions to generate at least one copy of a nucleic acid sequence complementary to the target sequence;
 (c) hybridizing the probe to the nucleic acid sequence complementary to the target sequence, so as to form a hybrid comprising the probe and the nucleic acid sequence complementary to the target sequence; and
 (d) detecting the hybrid as an indication of the presence of *Neisseria gonorrhoeae* in the test sample.

6. The method of claim 5 wherein said reaction mixture further comprises a control target polynucleotide and a control polynucleotide probe.

7. A kit comprising:
 (a) the primer/probe set of claim 5; and
 (b) amplification reagents.

8. The kit of claim 7 further comprising:
 (a) two or more polynucleotides each having a distinct nucleic acid sequence selected from the group consisting of SEQ ID NOs: 2, 4, 5, 6, 7, 10, and 11.

9. A method of detecting Neisseria gonorrhoeae in a test sample, said method comprising:
 (a) forming a reaction mixture comprising nucleic acid amplification reagents, a test sample potentially containing a *Neisseria gonorrhoeae* target sequence, and a primer/probe set according to claim 5;
 (b) subjecting the mixture to amplification conditions to generate at least one copy of a nucleic acid sequence complementary to the target sequence;
 (c) hybridizing the probe to the nucleic acid sequence complementary to the target sequence, so as to form a hybrid comprising the probe and the nucleic acid sequence complementary to the target sequence; and
 (d) detecting the hybrid as an indication of the presence of *Neisseria gonorrhoeae* in the test sample.

* * * * *

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      CT Forward Primer

<400> SEQUENCE: 1
gggattcctg taacaacaag tcagg                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      Preferred CT Forward Primer

<400> SEQUENCE: 2
gggattcdtg taacaacaag tcagg                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      More Preferred CT Forward Primer

<400> SEQUENCE: 3
gggattcgtg taacaacaag tcagg                                           25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      CT Reverse Primer

<400> SEQUENCE: 4
gcttgcacga agtactctag gag                                             23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      CT Probe
```

-continued

<400> SEQUENCE: 5
atagcactat agaactctgc aa                                              22

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      Alternative CT Probe

<400> SEQUENCE: 6
catagcacta tagaactctg caagcc                                          26

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      CT Beacon Probe

<400> SEQUENCE: 7
ctggcatagc actatagaac tctgcaagcc ag                                   32

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      NG Forward Primer

<400> SEQUENCE: 8
cgacgtaccg gtttttgttc                                                 20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      NG Reverse Primer

<400> SEQUENCE: 9
cggctcctta ttcggtttga cc                                              22

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      NG Probe

<400> SEQUENCE: 10
acaccgcccg gaacccga                                                   18

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      Alternative NG Probe

```
<400> SEQUENCE: 11
gaaacaccgc ccggaacccg at                                         22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      NG Beacon Probe

<400> SEQUENCE: 12
ctcggacacc gcccggaacc cgag                                       24
```